United States Patent
Schulz et al.

(10) Patent No.: US 6,582,663 B1
(45) Date of Patent: Jun. 24, 2003

(54) APPARATUS FOR TITRATION AND CIRCULATION OF GASES AND CIRCULATION OF AN ABSORBENT OR ADSORBENT SUBSTANCE

(75) Inventors: Robert Schulz, Ste–Julie (CA); Sabin Boily, Chambly (CA); Jacques Huot, Ste–Julie (CA)

(73) Assignee: Hydro-Quebec, Montreal (CA)

( * ) Notice: Subject to any disclaimer, the term of this patent is extended or adjusted under 35 U.S.C. 154(b) by 0 days.

(21) Appl. No.: 09/424,331

(22) PCT Filed: May 22, 1998

(86) PCT No.: PCT/CA98/00505

§ 371 (c)(1),
(2), (4) Date: Nov. 22, 1999

(87) PCT Pub. No.: WO98/53299

PCT Pub. Date: Nov. 26, 1998

(30) Foreign Application Priority Data

May 22, 1998 (CA) .............................................. 2207149

(51) Int. Cl.[7] .............................................. G01N 30/00
(52) U.S. Cl. .......................... 422/88; 73/865.5; 422/92; 422/103
(58) Field of Search .............................. 422/88, 83, 92, 422/103; 73/865.5

(56) References Cited

U.S. PATENT DOCUMENTS

| | | | |
|---|---|---|---|
| 3,349,625 A | * | 10/1967 | Benusa et al. |
| 3,850,040 A | * | 11/1974 | Orr, Jr. et al. ............. 73/865.5 |
| 4,305,291 A | * | 12/1981 | Nelson ....................... 73/865.5 |
| 5,109,716 A | * | 5/1992 | Ito et al. ...................... 73/865.5 |
| 5,239,482 A | * | 8/1993 | Ajot et al. ................... 364/497 |
| 5,591,897 A | * | 1/1997 | Nakamura et al. ...... 73/865.5 X |
| 5,895,841 A | * | 4/1999 | Lowell .................. 73/865.5 X |

FOREIGN PATENT DOCUMENTS

| | | |
|---|---|---|
| DE | 39 40 169 | 6/1991 |
| EP | 0 501 811 | 9/1992 |
| EP | 0 689 044 | 12/1995 |
| FR | 2 683 043 | 4/1993 |

OTHER PUBLICATIONS

B. Pommier et al, Bull. Soc. Chim. France 1972, 1268–1273.*

F. A. Shebl Sprechsaal 1977, 110, 466–470.*

(List continued on next page.)

*Primary Examiner*—Arlen Soderquist
(74) *Attorney, Agent, or Firm*—Foley & Lardner

(57) ABSTRACT

The invention concerns an apparatus for the titration and circulation of gases to determine metal hydride storing properties, with improved response time, greater dynamic range in terms of the usable amount of powder and the maximum pressure accessible and increased sensitivity. The invention also concerns a circulating apparatus considerably reducing the time for analysing and determining the properties of absorbent and adsorbent materials during a large number of adsorption-desorption cycles. Both sets of apparatus are provided with a reference tube inside their oven, near the sample-holder. Said sample-holder tube and reference tube are connected on either side of the differential pressure sensor, thereby considerably enhancing the overall performance of the titration system.

13 Claims, 14 Drawing Sheets

OTHER PUBLICATIONS

J. E. Shields et al, Am. Lab. 1984, 16, 81–82, 84, 86, 90–91.*
T. Ide et al, Fusion Technol. 1988, 14, 769–774.*
K. Nomura et al, Kagaku Gijutsu Kenkyusho Hokoku 1990, 85, 89–98.*
E. D. Snijder et al, J. CHem. Eng. Data 1994, 39, 405–408.*
G. Friedlmeier et al, J. Alloys Comp. 1995, 231, 880–887.*
H. Naono et al, Pharm. Tech. Jpn. 1996, 12, 235–244.*
H. Yayama et al, Kyushu Daigaku Kogaku Shuho 1981, 54, 421–425.*
L. J. Gillespie et al, J. Am. Chem. Soc. 1926, 48, 1207–1219.*
K. H. Lieser et al, Z. Physik. Chem. 1954, 202, 321–351.*
O. Boser J. Less–Common Met. 1976, 46, 91–99.*
R. Kadel et al, Ber. Bunsenges. Phys. Chem. 1978, 82, 1290–1302.*
N. Gerard et al, J. Phys. E: Sci. Instrum. 1979, 12, 476–477.*
R. L. Cohen et al, J. Less–Common Met. 1980, 70, 229–241.*
T. Hirata J. Less–Common Met. 1985, 107, 23–33.*
K. Yura et al, J. Chem. Soc., Faraday Trans. 2 1985, 82, 101–114.*
J. P. Manaud et al, J. Chim. Phys. Phys.–Chim. Biol. 1986, 83, 149–153.*
E Batalla et al, J. Mater. Res. 1986, 1, 765–773.*
G. Friedlmeier et al, Z. Phys. Chem. 1994, 183, 185–195.*

* cited by examiner

APPARATUS FOR TITRATION AND CIRCULATION OF GASES AND CIRCULATION OF AN ABSORBENT OR ADSORBENT SUBSTANCE

FIELD OF THE INVENTION

The present invention relates to an improved apparatus for the titration of gases, which can be used inter alia for the determination of the storage properties of metal hydrides.

The invention also relates to an apparatus hereinafter called "cycling apparatus", which permits to evaluate the behaviour of a substance when this substance is subjected to a large number of gas absorption/desorption cycles. This cycling apparatus can be used inter alia for evaluating the degradation of storage properties of a metal hydride subjected to cycles of hydrogen absorption/desorption.

BRIEF DESCRIPTION OF THE PRIOR ART

There are presently apparatuses especially devised for the titration of gases. These apparatuses are used in particular for determining the hydrogen absorption capacity and, therefore, the storage properties of metal hydrides. In the last case, they are particularly used for:

evaluating the storage capacity of metal hydrides as a function of the operating pressure (pressure=f(H/M) where H is the number of hydrogen atoms and M is the number of metal atoms); and evaluating the absorption and desorption kinetics (reaction dynamics) of the metal hydrides [H/M=f (time)].

FIG. 1 schematically illustrates the structure of an example of an existing apparatus used for the titration of hydrogen. This apparatus is disclosed in an article of Pascal TESSIER entitled "Hydrogen storage in metastable Fe—Ti" of 1995.

As can be noticed, this existing apparatus comprises a main duct 1' which is connected by a valve V3' to a source of hydrogen under pressure 5', and on which is mounted a pressure sensor (manometer) 7' for measuring the total pressure of hydrogen within the circuit.

The apparatus also comprises a first derivation duct 9' which connects the main duct via a valve V6' to a measuring chamber (13') having the shape of a tube in which can be introduced a sample of the substance for which he absorption or desorption properties are to be measured. The tube 13' is located in a furnace 11' having a temperature that can be adjusted at will as a function of the measurement to be carried out.

The apparatus further comprises a second derivation duct 15' having a first end 17' connected to the main duct 1' upstream of the connection between the same and the first derivation duct 9', and a second end 19' connected to the main duct downstream of the junction of the same with the first derivation duct. This second derivation duct 15' includes a small tank 21' of 50 cc and a differential pressure sensor 23'. A valve V11' is located in the main duct 1' between the junction 17' and the first derivation duct 9'. Two other valves V5' and V12' are respectively located on the second derivation duct 15' between, on the one hand, the tank 21' and the junction 17' and, on the other hand, the differential sensor 23' and the junction 19'.

Last of all, the apparatus comprises a third derivation duct 27' connecting a pump 29' via a valve VI' to the main duct 1' upstream of the junction 17'.

The valves mentioned hereinabove are operated by an informatized control system 33'. The two sensor pressures 7' and 23' are also connected to the control system. Most of the components of the apparatus are insulated in an isothermal enclosure 35' shown in dotted lines. A manual valve V10' is located in the derivation duct 9'. This manual valve V10' is kept permanently open except when the sample is inserted.

In use, after suitable calibration, one starts by creating a vacuum within the whole system by closing the valve V3' and by opening all the other valves to connect all the ducts, the sample carrying tube 13' and the tank 21' to the pump 29'. Then, all the valves are closed and the measurement up is bean by adjusting the hydrogen source to a given pressure. The valve V3' is opened and then closed. Subsequently, the valve V5', V11' and V12' are opened in series. After a pause, the valve V5' is closed and, after another pause, the valve V6' is opened and the measurement is carried out by measuring all the data given by both pressure sensors 7' and 23'.

This can be repeated several times with an increase in the hydrogen pressure, in order to obtain pressure/composition isotherm curves.

If the existing apparatuses for the titration of gases like the one disclosed hereinabove are efficient, they are subject to very stringent limitations in their use, because of their response time and the saturation of their differential pressure sensors, which reduces the limits of operation of the apparatus, its sensibility and the limits of detection of the same.

This problem is particularly important in that some metal hydrides like the nanocrystalline alloys disclosed in the following recently laid-open patent application Nos. CA-A-2,117,158 and WO-A-96/23906 naming the Applicant as one of the coowners, have very fast absorption and desorption kinetics.

From a practical standpoint, it is possible to increase the operating range of the apparatus by modifying the sequences of opening of the admission valves. However, the equilibrium time of the system is slower, which leads to a substantial lost of data at the beginning of each measurement.

Accordingly, there is presently a real need for an apparatus for the titration of gases where the response time would be improved and the differential pressure sensor would be less subject to saturation, with the major drawback that such limits generate, namely a diminution of the range of use of the apparatus, expressed in amount of metal hydride needed for a given sensitivity threshold and maximum working pressure, both in PCT mode [pressure=f(H/M)] and in dynamic mode [(H/M=f(time)].

On the other hand, there are presently no apparatus available on the market, at least to the knowledge of the Applicant, which would permit to carry out rapidly and in an efficient manner, titration measurements at two different pressures and two different temperatures, in order to characterize a substance like an hydride, and more precisely, the efficiency of this hydride when it is subjected to a large number of hydrogen absorption /desorption cycles.

It has already been proposed to use conventional titration apparatuses for this purpose. However, because of the delays that are relatively long for achieving furnace temperature equilibrium as well as the pressure equilibrium (a reequilibrium is required at reach cycle), these apparatuses are poorly adapted for cycling, where it is necessary to change the temperature of the furnace as well as the pressure quickly between each cycle during the course of measurements.

Therefore, there is also the need for a cycling apparatus which would permit to carry out absorption/desorption cycles at two temperatures and two operating pressures in a fast, efficient and performing manner.

SUMMARY OF THE INVENTION

The present invention satisfies the two needs mentioned hereinabove by providing:

on the one hand, a new apparatus for the titration of gases having an improved response time, a more important dynamics range relative to the amount of powder that is used and to the maximum operating pressure and an improved sensitivity; and on the other hand, a cycling apparatus allowing a substantial reduction of the time required for the analysis and determination of the properties of absorbing or desorbing materials during a large number of absorption/desorption cycles.

The apparatus according to the invention for the titration of a gas comprises:

a main duct (1) connected by a valve (V3) to a source of gas under pressure (5), said main duct being also connected to a first pressure sensor (7a);

a first derivation duct (9) connecting the main duct (1) via a valve (V6) to a sample carrying tube (13) which is located in a furnace (11) of adjustable temperature and is devised to receive a sample of a substance having gas absorption or adsorption/desorption properties to be measured;

a second derivation duct (15) having ends (17,19) connected to the main duct, at least one (19) of said ends being downstream of the first derivation duct (9), said second derivation duct connecting in series a valve (V5), a tank (21) and a differential pressure sensor (23);

a third derivation duct (27) connecting a pump (29) via a valve (V1) to the main duct (1);

an isothermal enclosure (35) for keeping the ducts and valves at a stable and controlled temperature; and a control system (33) for adjusting and controlling at will the temperature of the furnace (11), the pressure of the gas and the valves in real time.

This apparatus is characterized in that it further comprises:

a fourth derivation duct (37) connected via a valve (V7) to a reference tube (39) which has the same characteristics as the sample carrying tube and is located together with the same in the furnace (11), said fourth derivation duct being connected to the second duct (15) between the tank (21) thereof and the differential pressure sensor (23).

As can be appreciated, the titration apparatus according to the invention differs from the existing apparatuses in that it includes a reference tube within the furnace close to the sample carrying tube. The sample carrying tube and the reference tube are connected on both sides of the differential pressure sensor, thereby leading to a substantial increase in the general performances of the titration system.

Due to this structural difference, the titration apparatus according to the invention has three major advantages.

First of all, its range of use is wider with respect to the amount of powder and the maximum pressure that can be used.

Secondly, the sensitivity of measurements is increased (the limit of detection is improved).

Thirdly, its response time is faster (larger dynamics range and reduction in the equilibrium time required for the differential pressure sensor).

On the other hand, the apparatus according to the invention for the cycling of a gas absorbing/desorbing material, is characterized in that it comprises:

a furnace (111) with two compartments (171a, 171b) each having an adjustable temperature, said furnace being movable between two positions by suitable means (175);

a main duct (101) connected by a valve (V103) to the source of gas to be absorbed or adsorbed, this main duct being also connected to a pressure sensor (107);

a first derivation duct (109) connecting the main conduct (101) via a valve (V106) to a sample carrying tube (113) which is located within the furnace (111) in such a manner as to be always located in one of the compartments whatever be the position of the furnace, said sample carrying tube being in one of the compartments when the furnace is in one of its two positions, and in the other compartment when the furnace is in the other of its two positions;

two second derivation ducts (115a and 115b) independent from each other and connectable alternatively to the main duct (101) via two corresponding valves (V163a and 163b), each of said second derivation ducts (115) including a valve (V105), a tank (121) and a differential pressure sensor (123);

a third derivation duct (127) connecting a pump (129) via a valve (V101) to the main duct; and two fourth derivation ducts (137a and 137b) each connecting one of the second derivation ducts via a valve (V107a, V107b) to a reference tube (139), said reference tubes (139a and 139b) of these fourth derivation ducts being positioned within the furnace in such a manner as to be each positioned in one of the compartments of the furnace whatever be the position of the same, one of the reference tubes being always associated to the sample carrying tube whatever be the compartment in which the latter is located.

As it can again be understood, the cycling apparatus according to the invention comprises two furnaces and two enclosures that are kept under different hydrogen pressures, and are connected to a simple yet efficient computerized interface. It permits to quickly carry out measurements under two different pressures and at two different temperatures, and therefore to evaluate the degradation of the storage capacity of a substance like a metal hydride that is subjected to absorption/desorption cycles.

As previously indicated, one of the main applications of these two apparatuses is for evaluating in a more efficient and precise manner, the properties of recent hydrogen storage materials. This efficiency is due to the fact that these apparatuses are particularly well adapted for the measurement of very fast absorption/desorption kinetics.

However, it is worth mentioning that these apparatuses can also be used for numerous other applications, such as the absorption/desorption of other gases, the absorption, for example, of natural gas, the evaluation of the problems of oxidation and reduction of materials, etc.

The invention and its advantages will be better understood upon reading the following non-restrictive description of two preferred embodiments of the invention given with reference to test results.

DESCRIPTION OF TWO PREFERRED EMBODIMENTS OF THE INVENTION

Figure 2:
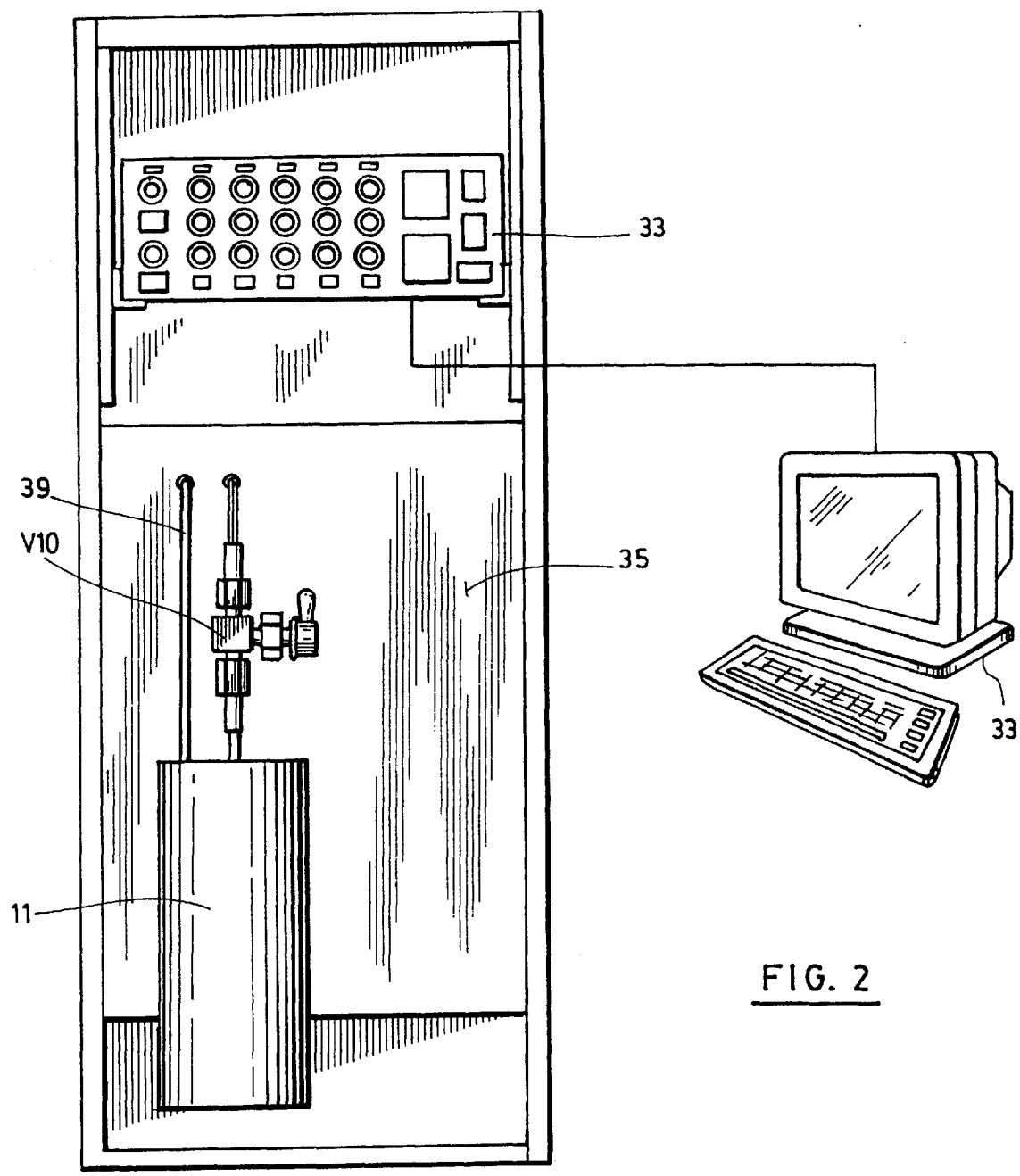
FIG. 2 is a general view of an apparatus according to the invention for the titration of gases.
Figure 3:
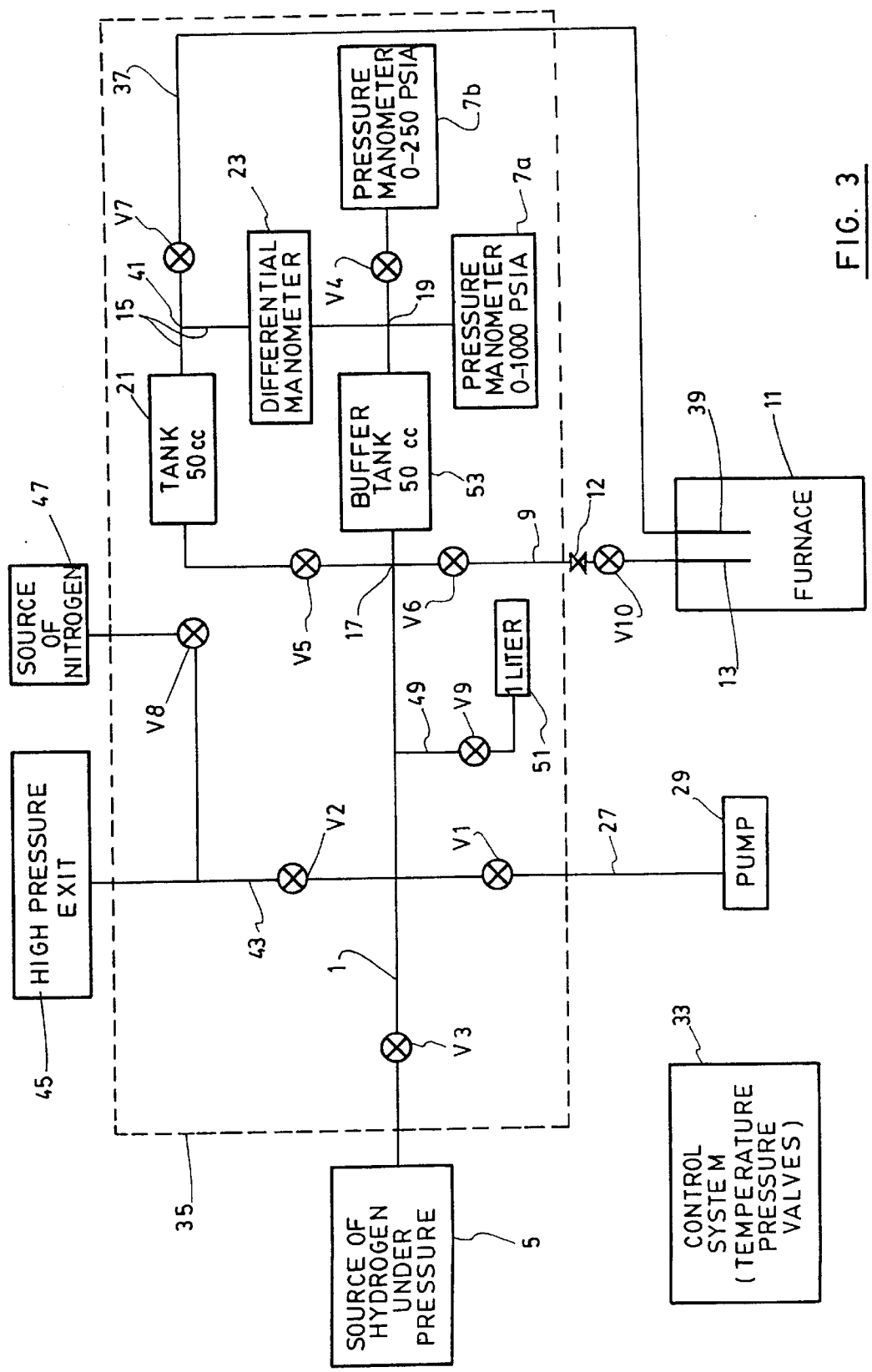
FIG. 3 is a schematic representation of the apparatus for the titration of gases shown in FIG. 2.

The apparatus according to the invention for the titration of gases as shown in FIGS. 2 and 3 comprises a main duct 1 connected by a valve V3 to a source 5 of gas under pressure. In the preferred embodiment hereinafter exemplified, this gas is hydrogen. However, the apparatus according to the invention could be used with any other kind of gas.

The main duct 1 is directly connected to a first pressure sensor (manometer) 7a capable of measuring pressures up to 1000 psia (6900 $kN/m^2$). It is also connected via a valve V4 to a second pressure sensor 7b that is more precise but capable of measuring pressure up to 250 psia only (1700 $kN/m^2$). It is worth mentioning that use will be made of the second sensor 7b when the pressure of the gas injected into the apparatus is lower than 250 psia. If this pressure is higher than 250 psia, the valve V4 will automatically close and only the sensor 7a will make the requested measurement of pressure.

The titration apparatus according to the invention also comprises a first derivation duct 9 connecting the main duct 1 via a valve V6 to a sample carrying tube 13 mounted in a detachable manner by means of a tightness connection 12 and provided with an internal temperature probe (not shown). This tube 13 is intended to receive a sample, the properties of the adsorption or absorption/desorption are to be measured. In use, this tube is located in a furnace 11 whose temperature can be adjusted and controlled at will. A manual valve V10 is located between the tightness connection 12 and the sample carrying tube 13. This valve is kept permanently opened, except when the tube 13 is being handled.

The titration apparatus according to the invention further comprises a second derivation duct 15. This duct has a first end 17 connected to the main duct substantially at the same level as the first derivation duct 9, and a second end 19 connected to the main duct at the same level or upstream of the pressure sensors 7a and 7b. This second derivation duct 15 includes a small tank 21 of 50 cc, and a differential pressure sensor 23.

The titration apparatus according to the invention still comprises a third derivation duct 27 for connecting a vacuum pump 29 via V1 to the duct 1, upstream of the junction 17.

Figure 1:
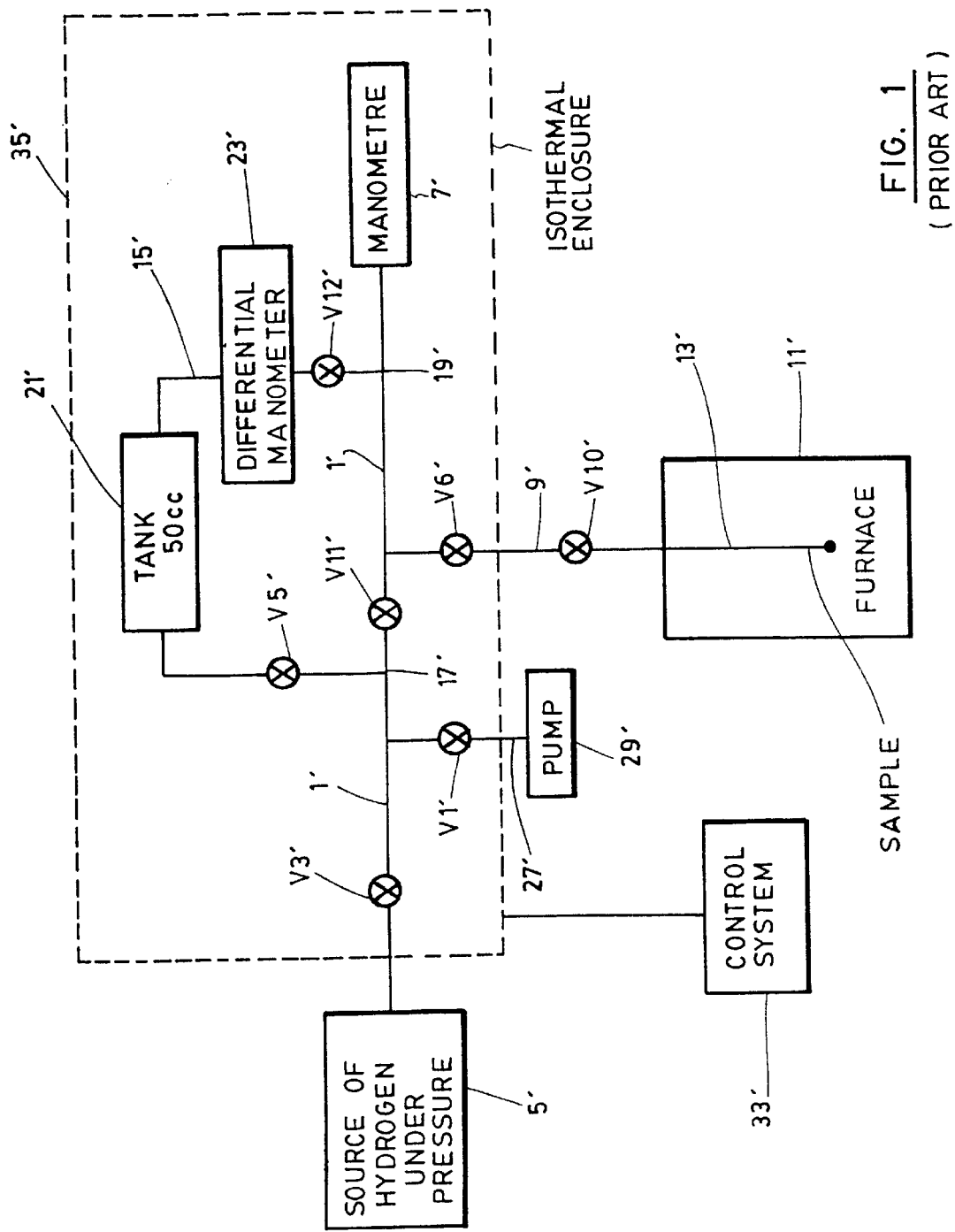
FIG. 1 identified as "prior art", is a schematic representation of an existing apparatus for the titration of gases.

Except for three minor differences, namely the absence of the valves V11' and V12" shown in FIG. 1 and the use of two pressure sensors 7a and 7b instead of a single one 7', the basic structure of the apparatus according to the invention is, so far, identical to the one of any existing titration apparatus.

The main structural feature distinguishing the invention over the state of the art lies in the presence of a fourth derivation duct 37. This duct connects the second derivation duct 15 via a valve V7 to a tube hereinafter called "reference tube" 39, which is located within the furnace 11 close to the sample-carrying tube 13. The reference tube has the same characteristics (structure, volume, . . . ) as the sample-carrying tube.

The junction 41 between the fourth derivation duct 37 and the second duct 15 is located between the tank 21 and the differential pressure sensor 23.

A fifth derivation duct 49 is connected to the main duct 1 upstream of the junctions of the same with the first and second derivation ducts 9 and 15. This fifth duct connects a large desorption tank 51 of 1 liter via a valve V9 to the main duct.

A sixth and last derivation duct 43 is connected to the main duct, substantially at the level of the junction of the same with the third derivation duct 27. This sixth duct 43 connects the main duct 1 via a valve V2 to a high pressure exit 45 and to a source 47 of inert gas under pressure, such as nitrogen, argon or helium. A valve V8 is located between this gas source 47 and the duct 43.

A small buffer tank 53 of 50 cc is advantageously located on the main duct between the junctions 17 and 19. This buffer tank 53 is used to compensate the differences in volume in the circuit resulting from the lengthy of each duct. Depending on the compensation to be carried out, which is easily determined during the calibration of the apparatus, the buffer tank can be filled with metal chunks to reduce its dead volume and, accordingly, adjust its residual volume to the difference of volume to be compensated within the ducts.

Like in the case of the existing apparatuses, most of the components of the apparatus according to the invention are kept insulated in an isothermal enclosure 35. The valves, the hydrogen and nitrogen sources, the pump, the high pressure exit and the temperature of the furnaces are controlled in real time by a computerized system 33 that is easily programmable.

The apparatus according to the invention for the titration of gases that has just been described, operates as follows.

After assembling the circuit, one proceeds to a calibration in order to determine the dead volume in the ducts between the valves and ensure that there is a same volume on both sides of the differential manometer during the measurements (as will be better understood hereinafter). During this first step, the buffer tank 53 is filled if necessary with chunks of iron or any other metal that does not absorb hydrogen. After having inserted the sample of metal hydride to be tested in the sample-carrying tube 13 and having closed valves V2 and V3 of the fifth and sixth derivation ducts, one may proceed to a purge of all the ducts. Then, the pump 29 is turn on and the valve V1 is opened. Thereafter, some other valves of the first, second and fourth derivation ducts 9, 15 and 37 are opened.

Then, the absorption measurements may be started. To do so, one may set the requested absorption pressures and temperature of the furnace 11. Then, the valves V6 and V7 leading to the sample-carrying tube 13 and to the reference tube 39 are closed while both of them are still under vacuum.

The valve V3 is opened and re-closed to connect all the ducts to the hydrogen source 5 and to place them under the requested absorption pressure. Once this is done, the valve V5 is closed and the valves V6 and V7 are simultaneously opened. Such creates a release of gas towards the tubes 13 and 39. Then, one may proceed to the simultaneous measurements of pressure by means of the sensors 7a and/or 7b and 23.

Once the measurements are completed, the high pressure exit 45 is operated and the valve V2 is opened after having closed the valves V6 and V7 in order to remove the hydrogen from the apparatus. Prior to opening the valve V2, one may open the valve V8 in order to mix nitrogen from the source 47 with the hydrogen that is evacuated from the apparatus. This improves the safety of the apparatus in use, by reducing the risk of fire.

Once the purge is completed, the desorption measurement can then be carried out.

To do so, the valve V9 of the fifth derivation duct is opened in order to connect the large tank 51 to the main duct. The extra volume provided by the tank "improves" the desorption. In this connection, one may understand that the average volume of the ducts and tubes on both sides of the differential sensor is of about 100 cc. By adding a volume of 1000 cc within the circuit, the dead volume for receiving the desorbed hydrogen is multiplied by 10. This increases the control of pressure increments.

After having adjusted the pressure in the main duct and closed the valve V5, one may then reopen again the valves V6 and V7 and carry out the required measurements with the pressure sensors 7a and/or 7b and 23.

Once everything is completed, the valve V6 can be closed again and one may either change the sample or starts another absorption and/or desorption measurement at different pressure and/or temperature.

As mentioned hereinabove, the apparatus for the titration of gases according to the invention, thanks to the presence of its reference tube close to the sample-carrying tube located within the furnace, has numerous advantages as compared to the existing apparatuses. Amongst these advantages, one may mention:

a wider range of operation in terms of amount of powder and maximum pressure that can be achieved;

an increased sensitivity; and an improved response time (wide dynamic range).

This apparatus is of simple use. In fact, its use is advantageously simplified and rendered more efficient and convivial thanks to the use of a computerized interface incorporated into its control system. This control software will not be described and claimed hereinabove.

Numerous tests were carried out on several prototypes at the Institut de Recherche d'Hydro-Québec (IREQ). Some of the results obtained during these tests are shown in FIGS. 4 to 8.

Figure 4:
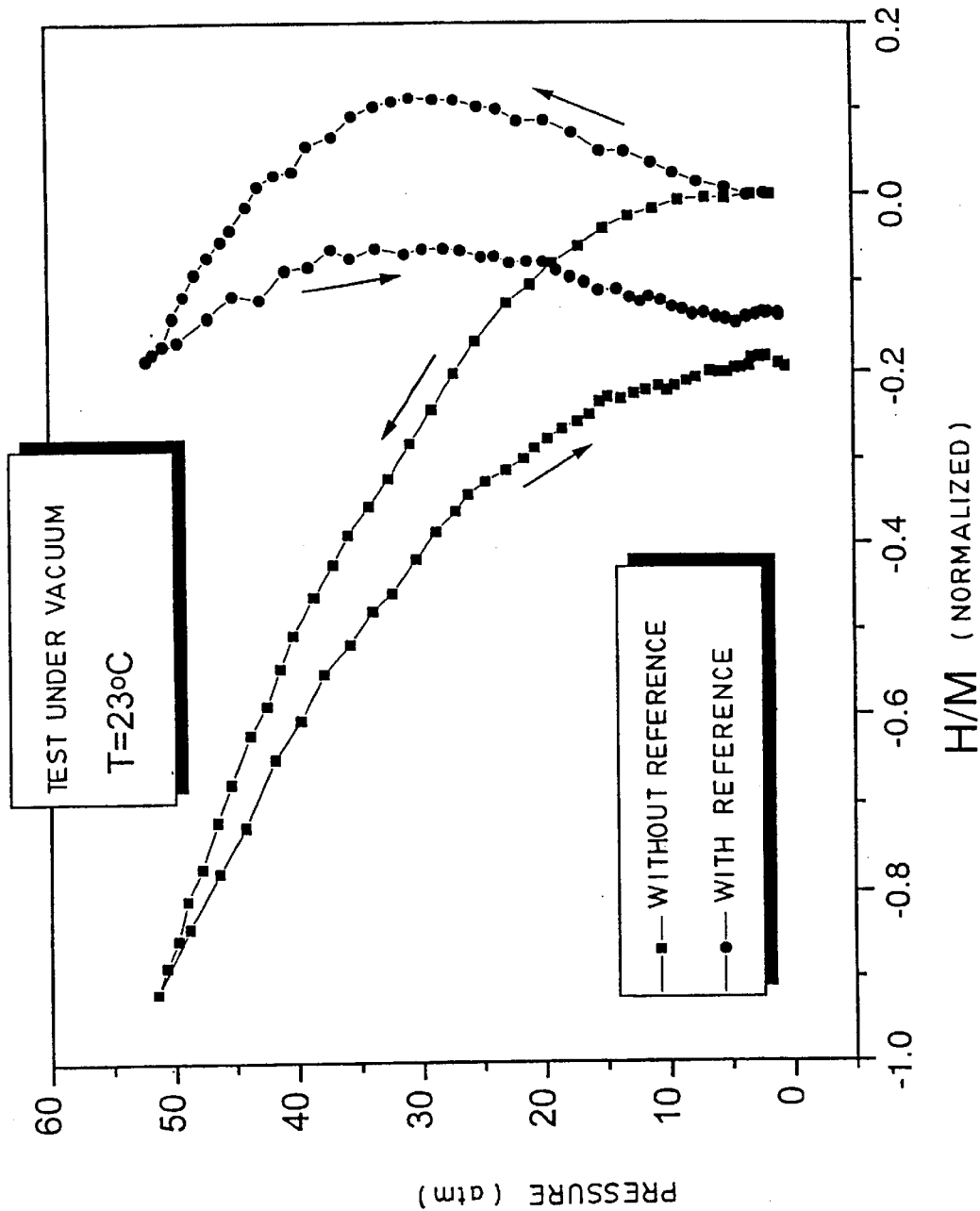
FIG. 4 is a PCT curve giving the value of the pressure measured without sample as a function of the ratio H/M measured and normalized when use is made of an existing apparatus as shown in FIG. 1 (■) and when use is made of an apparatus as shown in FIGS. 2 and 3 (●)
Figure 5:
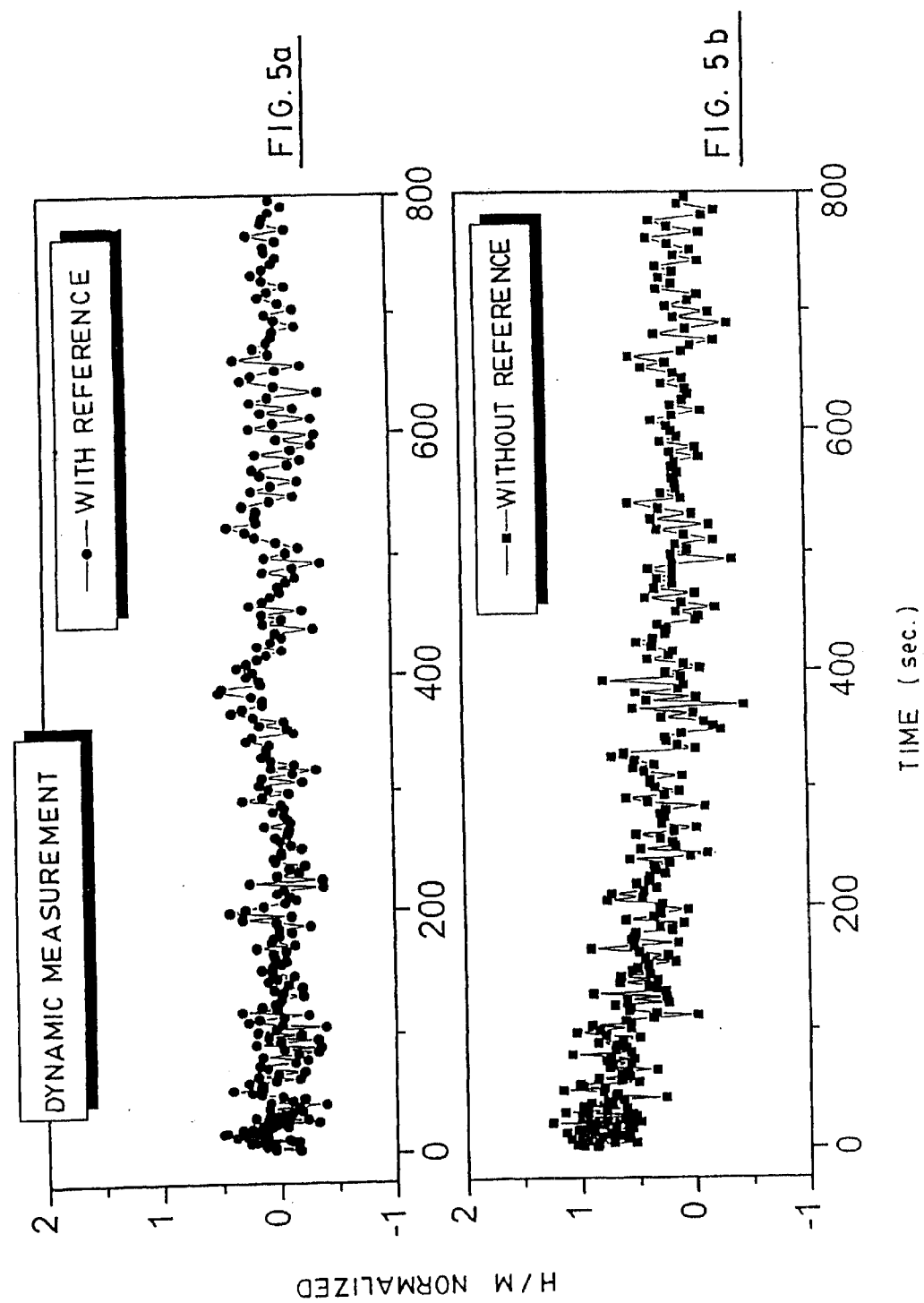
FIG. 5a is a (dynamic) kinetics curve giving the value of the ratio H/M measured without sample and normalised as a function of the time when use is made of an apparatus according to the invention.
FIG. 5b is a curve similar to the one of FIG. 5a, but obtained with an existing apparatus, without a reference tube within the furnace.

FIGS. 4 and 5 give PCT measurements [pressure=f(H/M)] and dynamic measurements carried out with an apparatus operating under vacuum (without sample) when this apparatus is provided with a reference tube (apparatus according to the invention) and when it does not have such a tube (existing apparatus).

As can be seen on FIG. 4, there is a substantial decrease in the variations of the H/M value with an empty cell when use is made of a reference tube (this improvement is of one order in magnitude). Also, as can be seen when comparing FIGS. 5a with 5b, there is also a very substantial decrease in the equilibrium time of the H/M value when use is made of a reference tube (this equilibrium time is reduced from more than 400 seconds without a reference tube to about 1 second with a reference tube). This last decrease is essential for the measurements of absorption/desorption carried out on metal hydrides that are very efficient, such as the nanocrystalline hydrides disclosed in the Canadian and international patent applications mentioned hereinabove, which have very fast absorption kinetics.

Figure 6:
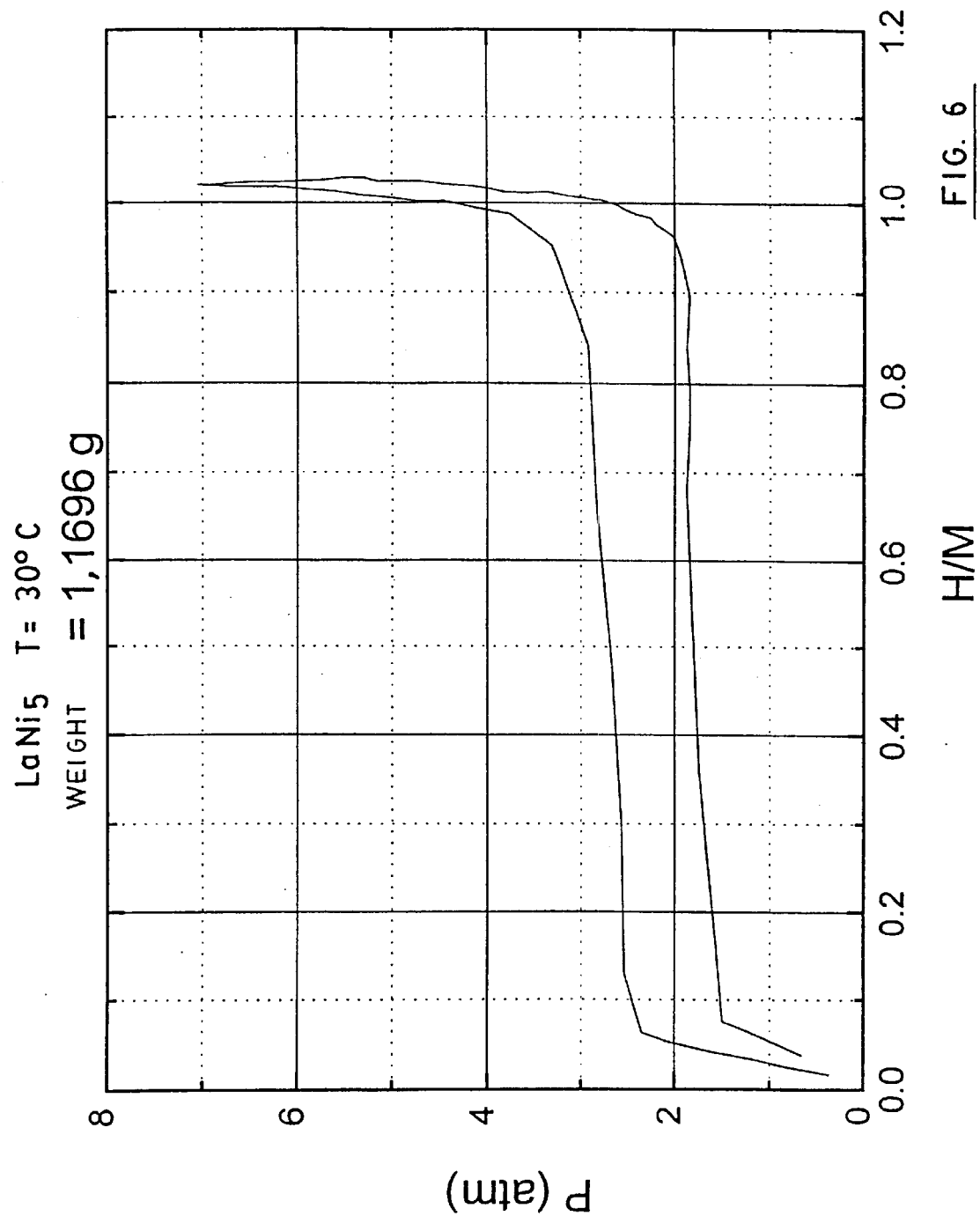
FIG. 6 is a PCT curve [(pressure=f (H/M)] obtained with an apparatus according to the invention on a sample of 1.1696 g of $LaNi_5$ at a temperature of 30° C.
Figure 7:
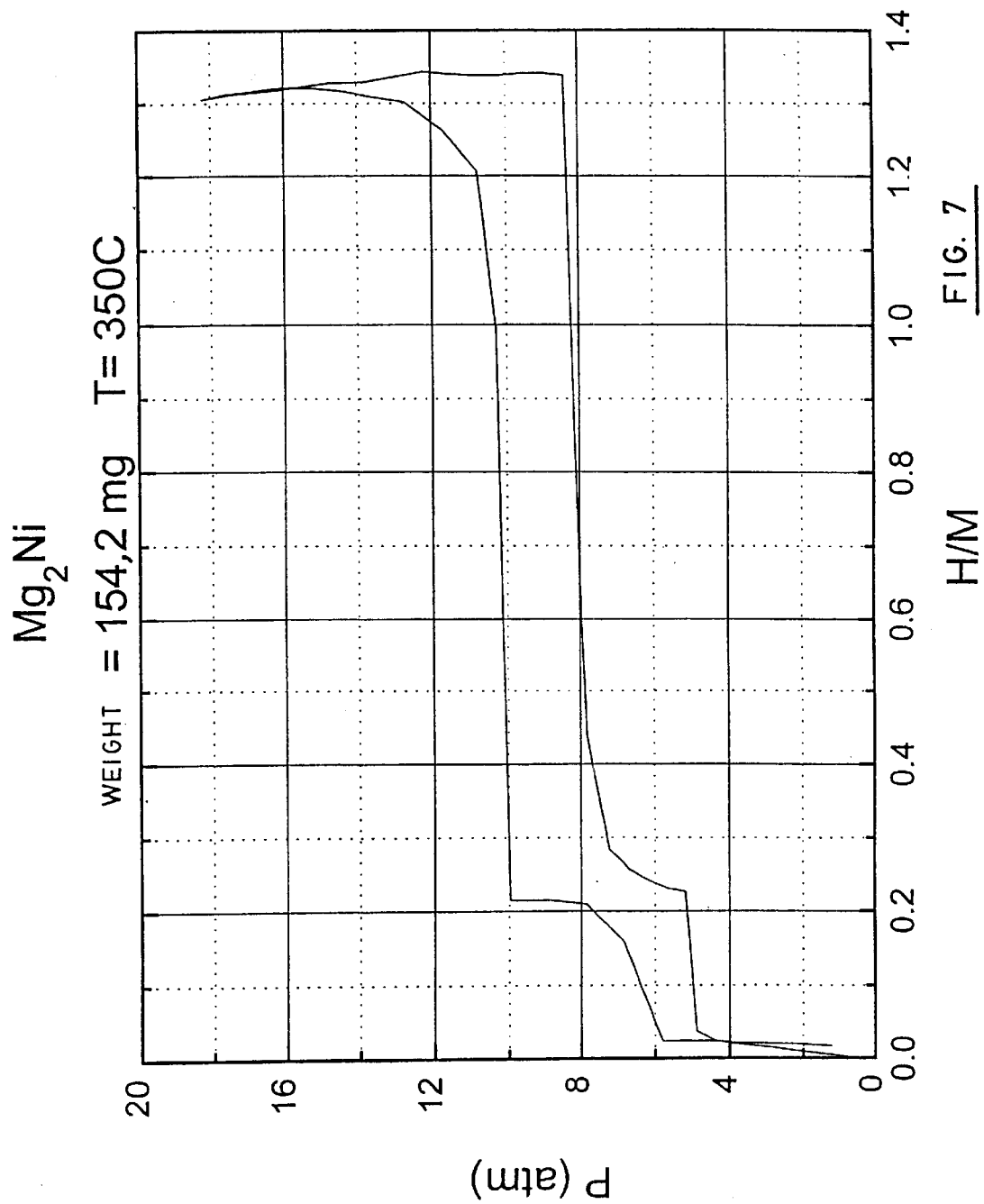
FIG. 7 is a PCT curve obtained with an apparatus according to the invention on a sample of 154.2 mg of $Mg_2Ni$ at the temperature of 350° C.
Figure 8:
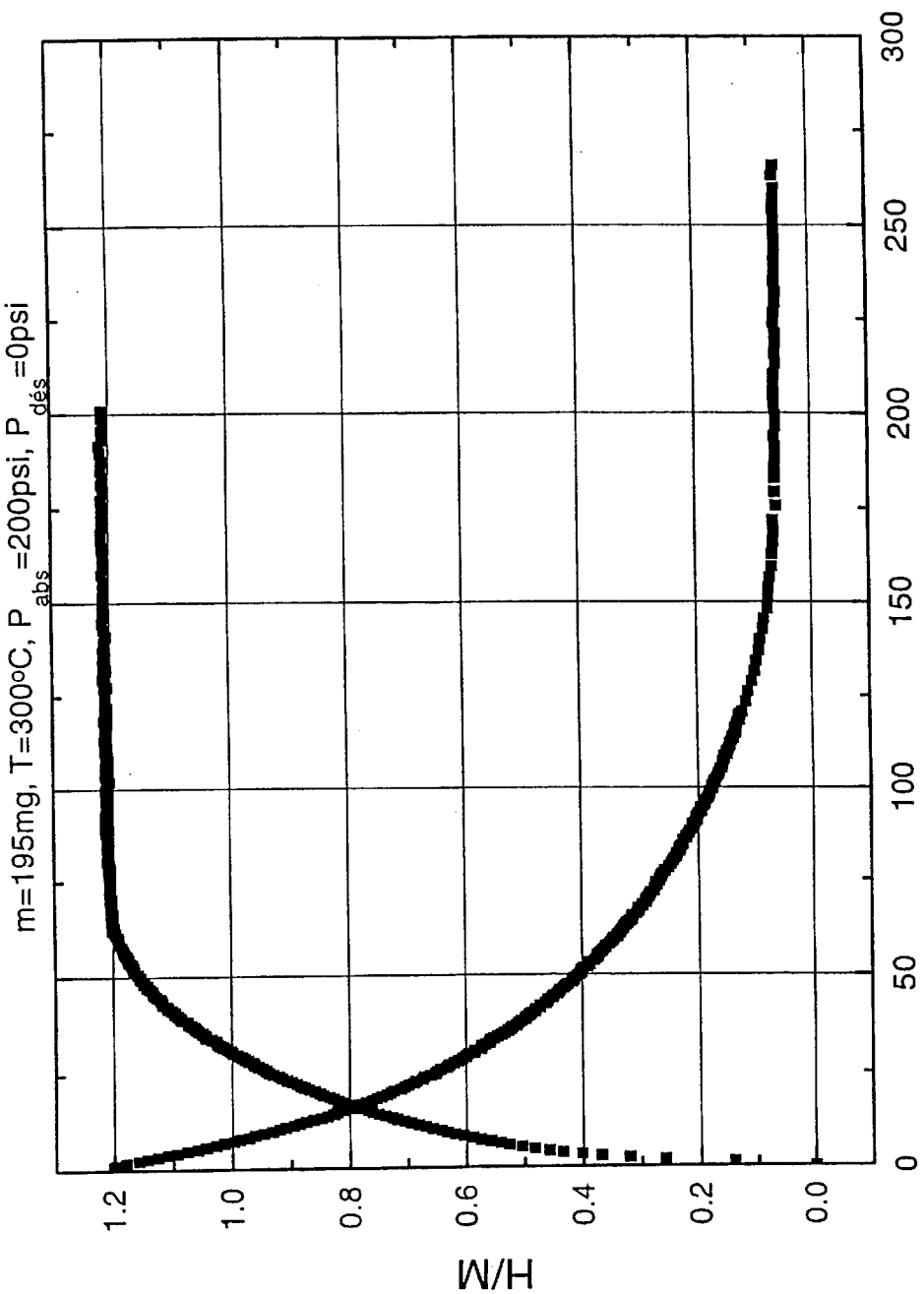
FIG. 8 is a dynamic curve [(H/M=f(time)] obtained with an apparatus according to the invention on a sample of 195 mg of a magnesium—based nanocrystalline material at a temperature of 300° C., the absorption pressure being 200 psi (1380 $kN/m^2$) and the pressure of desorption being 0 psi (0 $kN/m^2$)

FIGS. 6 and 8 are illustrative of the quality of the results that can be obtained with different types of samples of different weight at different temperatures.

Figure 9:
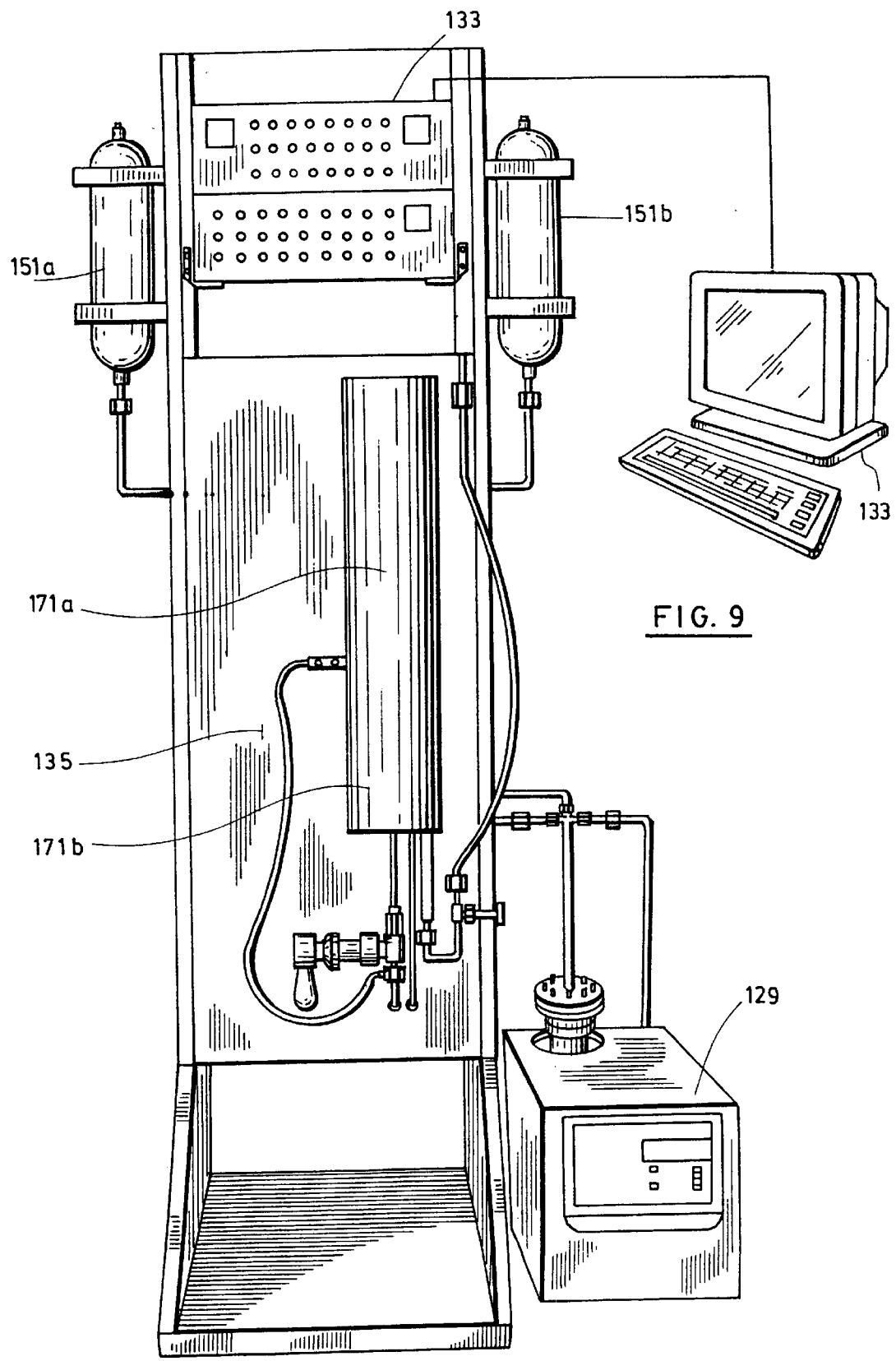
FIG. 9 is a general view of a cycling apparatus according to the invention.
Figure 10:
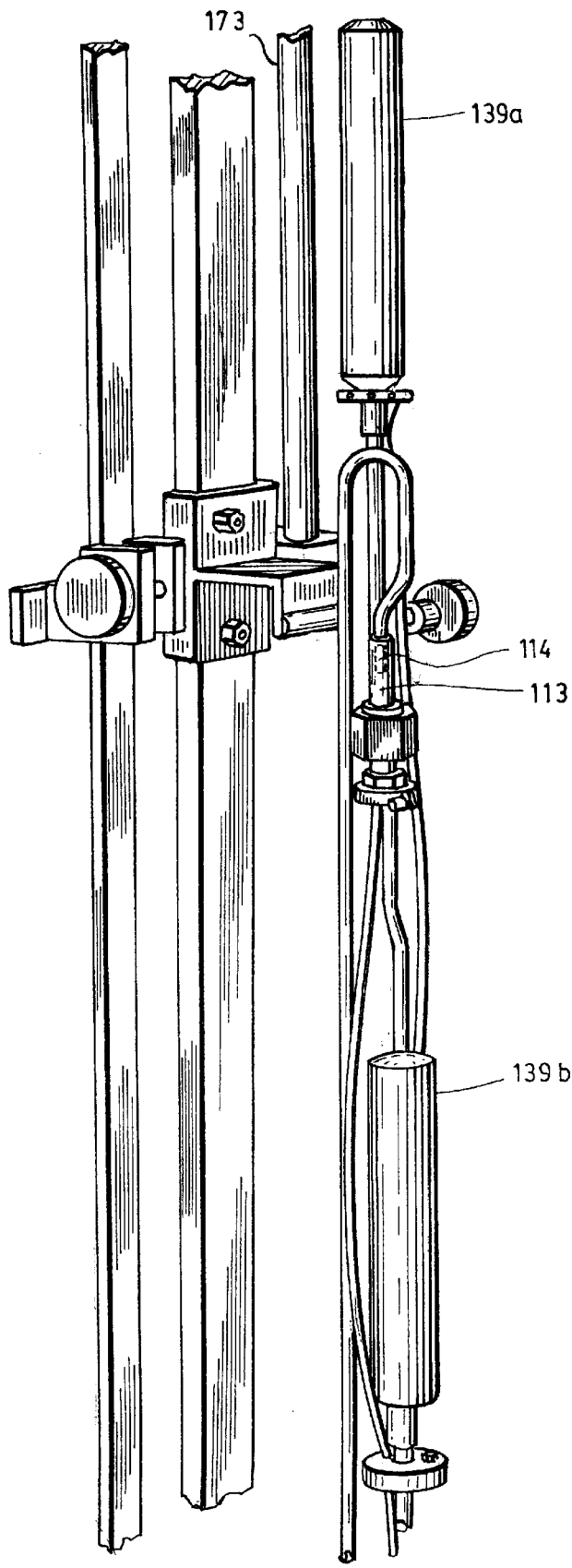
FIG. 10 is a view showing the guiding rail of the furnace, the two reference tanks and the sample carrying tube of the cycling apparatus shown in FIG. 9.
Figure 11:
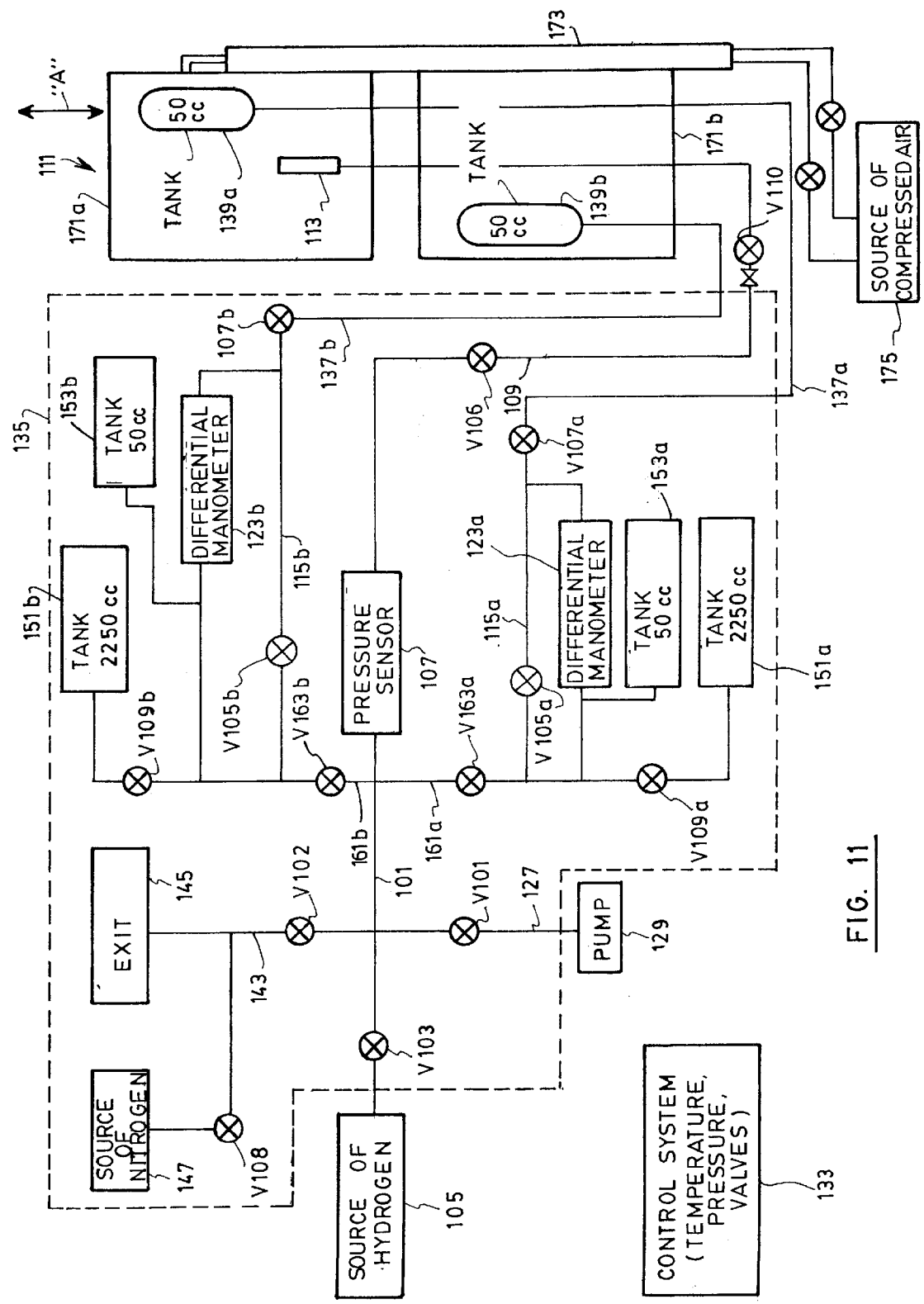
FIG. 11 is a schematic representation of the cycling apparatus shown in FIGS. 9 and 10.

The cycling apparatus according to the invention as shown in FIGS. 9, 10 and 11 derives directly from the titration apparatus that has just been described, except that it is devised to evaluate the characteristics of a gas-absorbing or -adsorbing material, and more precisely of a metal hydride, in order to determine the degradation of its storing properties when this material is subjected to a great number of absorption/desorption cycles. Once again, one will understand that the invention is not restricted to metal hydrides and that the same cycling apparatus could be used for evaluating the absorption capacities of any other kind of substance.

As it is better shown in FIG. 11, the cycling apparatus according to the invention has a basic structure very similar to the one of the titration apparatus previously disclosed. For this reason, all the identical structural components have been identified in the same way with the same reference numerals, to which has been added the number 100.

Thus, the cycling apparatus comprises a main duct 101 connected to a hydrogen source 105 via a valve V103. This main duct includes a pressure sensor 107.

A first derivation duct 109 connects the main duct 101 via valves V106 and V10 to a sample-carrying tube 113 that is mounted in a detachable manner by means of a tightening connection 112 and is provided with an internal temperature sensor 114 (see FIG. 10).

Two second derivation ducts 115a and 115b are connected to two branches 161a and 161b of the main duct, upstream the sensor pressure 107. These branches are respectively provided with valves V163a and V163b. These second ducts and their connections will be described hereinafter in greater detail.

A third derivation duct 127 connects the main duct to a vacuum pump 129.

Two fourth derivation ducts 137a and 137b including two valves V107a and V107b, respectively connect the second ducts 115a and 115b to two reference tubes 139a and 139b consisting of small tanks of 50 cc that are respectively positioned on top and below the sample-carrying tube 113.

Last of all, a further derivation duct 143 connects the main duct 101 to an exit device 145 via a valve V102. A nitrogen source 147 is connected via a valve V108 to this last duct 143 to mix the nitrogen with the gas exiting from the duct 143 and thus to reduce the risk of fire when this gas is inflammable.

Two large tanks 151a and 151b each with a dead volume of 2.25 liters, are respectively connected by valves V109a and V109b to the second ducts 115a and 115b. One may understand that the volume of these tanks may of course be modified at will.

Valve 105a and 105b and differential pressure sensors 123a and 123b are mounted in series on the second ducts 115a and 115b.

Last of all, two small tanks 121a and 121b of 50 cc each are respectively connected to the second derivation ducts 115a and 115b between the valves V105a and V105b and the differential pressure sensors 123a and 123b.

As can now be noticed, each of the second derivation conducts 115a and 115b to which a reference tube 139a or 139b, is associated is identical in terms of structure and operation to the circuit formed by the second, fourth and fifth derivation ducts 15, 37 and 49 of the titration apparatus previously described. The only difference lies in that these second ducts 115a and 115b are connectable in an alternative manner directly to the main duct 101 by means of a valve V161a and V161b, this being of course essential to obtain the requested cycling.

One will therefore understand that the sequence of operation is absolutely identical to the one that has already been described in detail, except that, when the reference tube 139a is used for a measurement, the valve V163b is closed for isolating the second duct 115b and all the elements associated to the same, whereas, when the reference tube 139b is used, then the valve V163a is closed.

Most of the components disclosed hereinabove are located in an isothermal enclosure 135 and connected to a control system 133.

To induce the variation of temperature during cycling, the furnace 111 in which the sample-carrying tube 113 and the reference tubes 139a and 139b are located, may have two compartments 171a and 171b that are coaxial. The temperature of each compartment can be adjusted and controlled independently from the other. These two compartments are mounted onto a jack 173 connected to a source of compressed air 175 and actionable at a distance by means of the same. For each cycle, the jack 173 moves together both compartments of the furnace 111 upwardly or downwardly, as shown by the arrow A. In lower position, which is the one illustrated in FIG. 11, the sample-carrying tube 113 and the reference tube 139a are both in the compartment 171a. Then, the requested absorption/desorption is carried out inside this compartment 171a at the temperature of the same, by opening the second duct 115a. In upper position, the sample carrying tube 113 is with the reference tube 139b in the compartment 171b. Then, the requested desorption/absorption is carried out at the temperature of the compartment 171b, by opening the second conduct 115b.

As can therefore be appreciated, the cycling apparatus according to the invention uses a furnace with two compartments as well as two pressure enclosures for the absorption and desorption. Such permits to substantially reduces the time required for evaluating the cycling properties of absorbing materials such as metal hydrides.

Tests were carried out on the prototype of a cycling apparatus as previously described. Some of the obtained results are reported in FIGS. 12 to 14.

Figure 12:
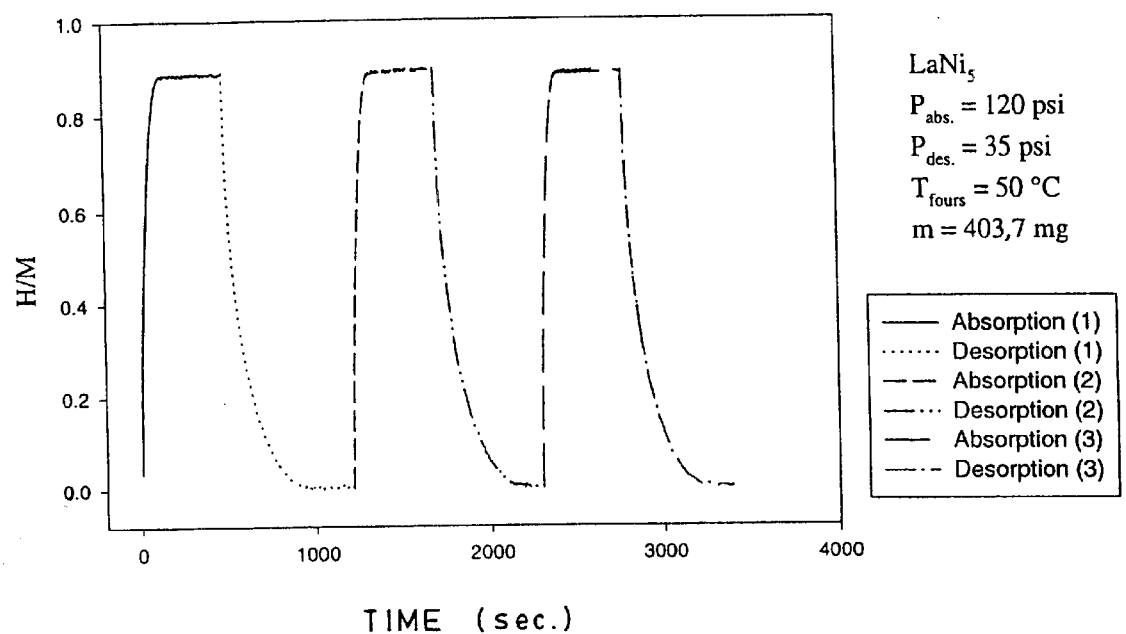
FIG. 12 is a dynamic cycling curve measured with the apparatus shown in FIGS. 9 to 11 on a sample of 403.7 mg of $LaNi_5$, this curve giving the value of the ratio H/M as a function of the time under an absorption pressure of 120 psi (830 $kN/m^2$) and a desorption pressure of 35 psi (240 $kN/m^2$), both compartments of the furnace being kept at 50° C.

FIG. 12 is a dynamic cycling curve [H/M=f(time)] obtained with a sample of $LaNi_5$. This curve illustrates quite well the repetition of cycles. In this case, both compartments of the furnace were maintained at the same temperature of 50° C.

Figure 13:
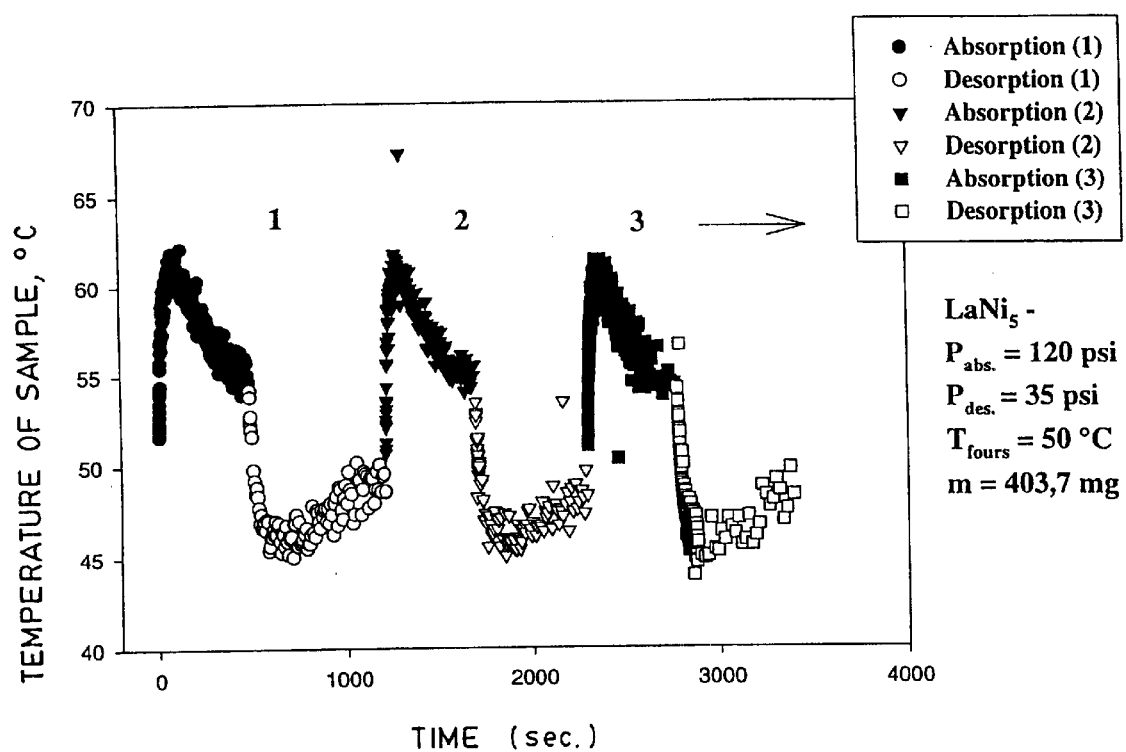
FIG. 13 is a cycling curve measured with the apparatus shown in FIGS. 9 to 11 on a sample of 403.7 mg of $LaNi_5$, this curve giving the temperature of the sample as a function of the time under an absorption pressure of 120 psi (830 $kN/m^2$) and a desorption pressure of 35 psi (240 $kN/m^2$), both compartments of the furnace being kept at 50° C.

FIG. 13 is a cycling curve giving the value of the temperature of a sample of $LaNi_5$ as a function of the time. Once again, both compartments were kept at the same temperature of 50° C. This curve shows that the temperature of the sample varies in a substantial manner during the absorption/desorption cycles.

Figure 14:
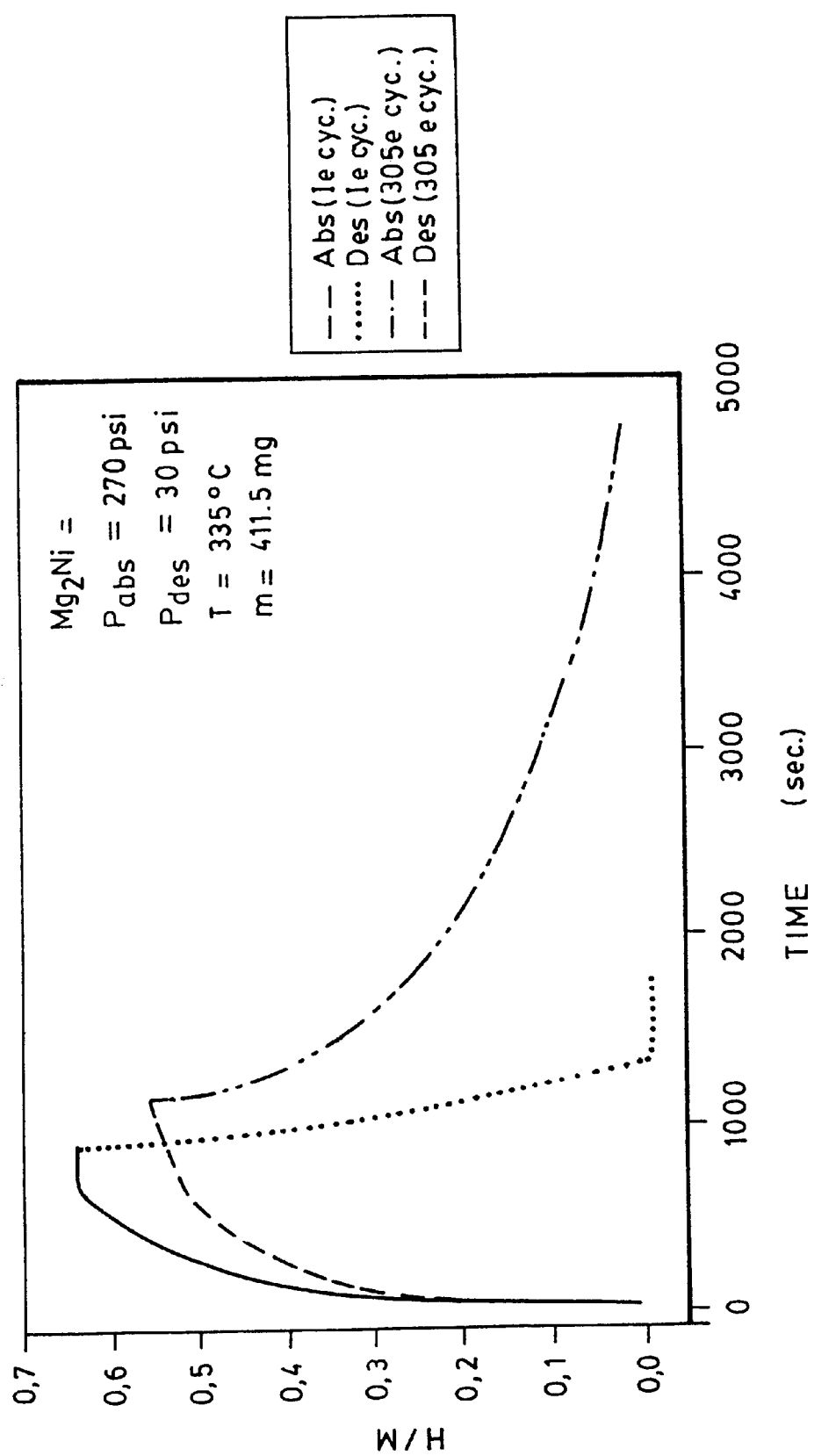
FIG. 14 is a curve giving the value of the ratio H/M as a function of the time during the first and 350 cycles of absorption/desorption of a sample of 411.5 mg of $MgNi_5$, the values being measured with the apparatus shown in FIGS. 9 to 11, under an absorption pressure of 270 psi (1860 $kN/m^2$) and a desorption pressure of 30 psi (205 $kN/m^2$), both compartments of the furnace being kept at 335° C.

Last of all, FIG. 14 is a dynamic curve showing the difference of behaviour of a sample of $Mg_2Ni$ between the first and 305th cycles of absorption/desorption. As can be seen, the material looses about 15% of its hydrogenation capacity and is subjected to a substantial degradation of its desorption kinetics in use.

Of course, numerous modifications could be made to the embodiments that just have been described without departing the scope of the present invention as defined in the appended claims. Thus, one may understand that use could easily be made of temperatures of higher or lower than those described in this document. Use could also be made of, for example, a refrigerator for absorption at low temperature, while the desorption at high temperature could always be carried out in a furnace. Therefore, there is possibility of using other alternative methods of desorption or absorption.

What is claimed is:

1. An apparatus for the titration of a gas, of the type comprising:
   a main duct connected by a first valve to a source of gas under pressure, said main duct being also connected to a first pressure sensor;
   a first derivation duct connecting the main duct via a second valve to a sample carrying tube which is located in a furnace of adjustable temperature and is devised to receive a sample of a substance having gas absorption or adsorption/desorption properties to be measured;
   a second derivation duct having first and second ends connected to the main duct, said second derivation duct connecting in series a third valve, a first tank and a differential pressure sensor;
   a third derivation duct connecting a pump via a fourth valve to the main duct;
   an isothermal enclosure for keeping the ducts and valves at a stable and controlled temperature; and
   a control system for adjusting and controlling at will the temperature of the furnace, the pressure of the gas and the valves in real time;
   said apparatus being characterized in that it further comprises:
      a fourth derivation duct connected via a fifth valve to a reference tube which has the same characteristics as the sample carrying tube and is located together with the same in the furnace, said fourth derivation duct being connected to the second duct between the first tank thereof and the differential pressure sensor; and a buffer tank mounted onto the main duct between the first and second ends of the second derivation duct, said buffer tank being filled up with metal chunks to reduce its dead volume, and used for compensating any difference in volume in the main and derivation ducts.

2. An apparatus as defined in claim 1, characterized in that it further comprises:

a fifth derivation duct connected to the main duct upstream the first and second derivation ducts, this fifth derivation duct being connected to a second tank via a sixth valve, said second tank being used for the desorption by increasing substantially the dead space of the duct when the sixth valve is open.

3. An apparatus as defined in claim 2, characterized in that it further comprises:

a sixth derivation duct connected to the main duct, said sixth derivation duct being connected to a gas outlet via a seventh valve.

4. An apparatus as defined in claim 3, characterized in that it further comprises:

a source of inert gas connected via an eighth valve to the sixth derivation duct for mixing the inert gas with the gas exiting through this sixth derivation duct and thus reducing the risk of fire when this gas is inflammable.

5. An apparatus as defined in claim 1, characterized in that it further comprises:

a second pressure sensor connected to the main duct via a ninth valve, this second sensor being adapted to measure pressures up to a maximum pressure which is lower than the maximum pressure which can be measured by said first pressure sensor.

6. A process for evaluating the hydrogen storage capacity of a metal hydride as a function of the operating pressure (pressure=f(H/M), where H is the number of hydrogen atoms and M is the number of metal atoms), which comprises:

calibrating an apparatus as claimed in claim 1, in order to determine the dead volume in the ducts between the valves;

inserting a sample of said metal hydride to be tested in the sample carrying tube, closing the first valve and proceeding to a purge of all the ducts;

turning on the pump and opening the valves of the first, second and fourth derivation ducts;

setting the requested absorption pressure and temperature of the furnace and closing the second and the fifth valves leading to the sample, the carrying tube and the reference tube while both of said tubes and are still under vacuum;

opening the first valve and reclosing it to connect all the ducts to the source of gas, said gas being hydrogen, and thus to place all of ducts under the requested absorption pressure;

closing the third valve and simultaneously opening the second and the fifth valves to create a release of gas towards the carrying tube and the reference tube proceeding to a simultaneous measurement of pressure by means of the first pressure sensor and the differential pressure sensor;

closing the second and the fifth valves and opening the seventh valve to remove hydrogen from the apparatus;

adjusting the pressure in the main duct, closing the fifth valve and reopening again the second and the fifth valves;

proceeding to another measurement of pressure by means of the first pressure sensor and the differential pressure sensor; and closing the second valve prior to reusing the apparatus.

7. A process for evaluating the hydrogen absorption and desorption kinetics of a metal hydride (H/M=f(time), where H is the number of hydrogen atoms and M is the number of metal atoms), which comprises calibrating an apparatus as claimed in claim 1, in order to determine the dead volume in the ducts between the valves;

inserting a sample of said metal hydride to be tested in the sample carrying tube, closing the first valve and proceeding to a purge of all the ducts;

turning on the pump and opening the valves of the first, second and fourth derivation ducts;

selecting one of two furnace positions and setting the requested absorption pressure and temperature of the furnace and closing the second and the sixth valves leading to the sample, the sample carrying tube and the reference tube while all of said tubes are still under vacuum;

opening the first valve and reclosing it to connect all the ducts to the source of gas, said gas being hydrogen, and thus to place all of the ducts under the requested absorption pressure;

closing the third valve and simultaneously opening the second and the sixth valves to create a release of gas towards the sample carrying tube and the reference tubes; and proceeding to a simultaneous measurement of time and of pressure by the pressure sensor.

8. A cycling apparatus for evaluating the behaviour of a gas absorbing of adsorbing substance when this substance is subjected to a large number of absorption/desorption cycles, characterized in that it comprises:

a furnace with two compartments each having an adjustable temperature, said furnace being movable between two positions by suitable means;

a main duct connected by a first valve to a source of gas to be absorbed or adsorbed, this main duct being also connected to a pressure sensor;

a first derivation duct connecting the main duct via a second valve to a sample carrying tube which is located within the furnace in such a manner as to be always positioned in one of the compartments whatever be the position of the furnace, said sample carrying tube being in one of the compartments when the furnace is in one of its two positions, and in the other compartment when the furnace is in the other of its two positions;

two second derivation ducts independent from each other, each of said second derivation ducts connectable alternatively to the main duct via a corresponding third valve and connecting in sequence an inlet, a fourth valve, a first tank, a differential pressure sensor and an outlet;

a third derivation duct connecting a pump via a fifth valve to the main duct; and two fourth derivation ducts each connecting the outlet of one of the second derivation ducts via a sixth valve to a reference tube, said reference tubes of these fourth derivation ducts being positioned within the furnace in such a manner as to be each positioned in one of the compartments of the furnace whatever be the position of the same, one of the reference tubes being always associated to the sample carrying tube whatever be the compartment in which the latter is located.

9. An apparatus as claimed in claim 8, characterized in that it further comprises:

two second tanks respectively connected via a seventh valve to the second derivation ducts, these second tanks helping the desorption by substantially increasing the dead space of the ducts when the seventh valve are opened.

10. An apparatus as claimed in claim 9, characterized in that it further comprises:

a fifth derivation duct connected to the main duct said other derivation duct being connected to a gas exit via an eighth valve.

11. An apparatus as defined in claim 10, characterized in that it further comprises:

a source of inert gas connected via a ninth valve to the fifth derivation duct for mixing the inert gas with the gas exiting through the fifth derivation duct and thus for reducing the risk of fire when this gas is inflammable.

12. An apparatus as defined in claim 8, characterized in that it further comprises:

an internal temperature sensor located within the sample carrying tube.

13. A process for evaluating the hydrogen adsorption and desorption kinetics of a metal hydride as a function of the time (H/M=f (time) where H is the number of hydrogen atoms and M is the number of metal atoms), which comprises:

calibrating an apparatus as claimed in claim 8, in order to determine the dead volume in the ducts between the valves;

inserting a sample of said metal hydride to be tested in the sample carrying tube, closing the first valve and proceeding to a purge of all the ducts;

turning on the pump and opening the valves of the first, second and fourth derivation ducts;

setting the requested absorption pressure and temperature of the furnace and closing the second and the fifth valves leading to the sample, the carrying tube and the reference tube while both of said tubes and are still under vacuum;

opening the first valve and reclosing it to connect all the ducts to the source of gas, said gas being hydrogen, and thus to place all of ducts under the requested absorption pressure;

closing the third valve and simultaneously opening the second and the fifth valves to create a release of gas towards the carrying tube and the reference tube proceeding to a simultaneous measurement of pressure by means of the first pressure sensor and the differential pressure sensor;

closing the second and the fifth valves and opening the seventh valve to remove hydrogen from the apparatus;

adjusting the pressure in the main duct, closing the fifth valve and reopening again the second and the fifth valves;

proceeding to another measurement of pressure by means of the first pressure sensor and the differential pressure sensor; and closing the second valve prior to reusing the apparatus.

* * * * *